United States Patent [19]

Sloboda et al.

[11] 4,197,312

[45] * Apr. 8, 1980

[54] ALKALI METAL AND ALKALINE EARTH METAL SALTS OF BENZOYLACETONITRILES

[75] Inventors: Adolph E. Sloboda, New City; John W. Hanifin, Jr., Suffern, both of N.Y.

[73] Assignee: American Cyanamid Company, Stamford, Conn.

[*] Notice: The portion of the term of this patent subsequent to Apr. 11, 1995, has been disclaimed.

[21] Appl. No.: 904,354

[22] Filed: May 9, 1978

[51] Int. Cl.$^2$ .................. A61K 31/275; A61K 31/28; A61K 31/33

[52] U.S. Cl. ............................. 424/304; 260/326.5 R; 260/429 R; 260/429.9; 260/438.1; 260/439 R; 260/448 R; 260/465 E; 260/465 F; 424/248.57; 424/250; 424/267; 424/274; 424/287; 424/289; 424/294; 424/295; 544/107; 544/398; 546/230

[58] Field of Search ...................... 424/304, 289, 294; 260/465 F, 465 E, 429.9, 438.1

[56] References Cited

U.S. PATENT DOCUMENTS

| | | | |
|---|---|---|---|
| 3,763,285 | 10/1973 | Riebel et al. | 260/465 F X |
| 3,775,517 | 11/1973 | Riebel et al. | 260/465 F X |
| 4,083,993 | 4/1978 | Sloboda et al. | 424/304 |

FOREIGN PATENT DOCUMENTS 2302273 7/1974 Fed. Rep. of Germany .
2409462 10/1975 Fed. Rep. of Germany .

OTHER PUBLICATIONS

Dorsch et al., J.A.C.S., 54 (1932), pp. 2960–2964.
C.A., 69 (1968), Pihl et al., 100208s.
Nakanishi et al., J. Med. Chem., 16(3), 1973, pp. 214–219.

*Primary Examiner*—Joseph Paul Brust
*Attorney, Agent, or Firm*—E. A. Conroy, Jr.

[57] ABSTRACT

This disclosure describes new compounds and compositions of matter useful as anti-inflammatory agents and as inhibitors of the progressive joint deterioration characteristic of arthritic disease and the methods of meliorating inflammation and of inhibiting joint deterioration in mammals therewith, the novel active ingredients of said compositions of matter being the pharmacologically acceptable cationic salts of benzoylacetonitrile, o-fluorobenzoylacetonitrile, m-fluorobenzoylacetonitrile, p-fluorobenzoylacetonitrile, or mixtures thereof.

3 Claims, No Drawings

ALKALI METAL AND ALKALINE EARTH METAL SALTS OF BENZOYLACETONITRILES

BRIEF SUMMARY OF THE INVENTION

This invention relates to new organic compounds and, more particularly, is concerned with the novel pharmacologically acceptable cationic salts of certain benzoylacetonitriles which may be represented by the following structural formula:

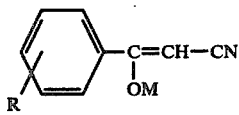

wherein R is hydrogen or fluoro and M is a pharmaceutically acceptable cation. The invention also includes novel compositions of matter containing the above defined salts and the methods of meliorating inflammation and of inhibiting joint deterioration in mammals therewith. Benzoylacetonitrile and o-fluorobenzoylacetonitrile have been described by Dorsch et al., J.A.C.S. 54, 2960 (1932) and by Nakanishi et al., J. Med. Chem., 16(3), 214 (1973), respectively; whereas m-fluorobenzoylacetonitrile and p-fluorobenzoylacetonitrile have both been described by Pihl et al., Reakts. Sposobnost Org. Soedin. Tartu. Gos. Univ., 5(1), 27 (1968).

DETAILED DESCRIPTION OF THE INVENTION

The useful pharmaceutically acceptable salts of the above structural formula are those with pharmacologically acceptable metal cations, ammonium, amine cations, or quaternary ammonium cations. Preferred metal cations are those derived from the alkali metals, e.g. lithium, sodium and potassium, and from the alkaline earth metals, e.g. magnesium and calcium, although cationic forms of other metals, e.g. aluminum, zinc, iron and in particular copper, are within the scope of the invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and arylaliphatic amines containing up to and including 18 carbon atoms, as well as heterocyclic amines, e.g. piperidine, morpholine, pyrrolidine, piperazine and lower alkyl derivative thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl)diethanolamine. Examples of suitable pharmacologically acceptable quaternary ammonium cations are tetramethylammonium, tetraethylammonium, benzyltrimethylammonium, phenyltrimethylammonium, and the like.

The novel cationic salts of the present invention may exist in both cis and trans forms as follows:

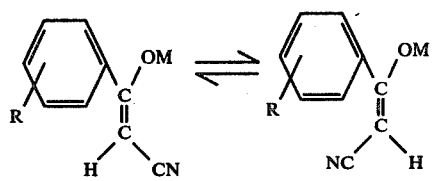

The novel compounds of the present invention may be readily prepared as set forth in the following reaction scheme:

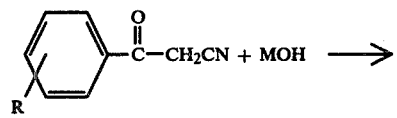

wherein R and M are as hereinabove defined. This reaction is best carried out in water or lower alkanols or mixtures thereof at ambient temperatures. Concentration of the reaction mixture followed by lyophilization or dilution with a non-polar solvent (e.g., acetone, methyl isobutyl ketone, dimethylformamide, etc.) provides the desired product.

The novel compounds of the present invention have been found to be highly useful for meliorating inflammation and inhibiting joint deterioration in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gm. to about 7.0 gm. of the active ingredient for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active ingredient may be administered in any convenient manner such as by the oral, intravenous, intramuscular, topical, intra-articular, or subcutaneous route. The antiinflammatory activity of the novel compounds of the present invention was established by the following test.

Adjuvant induced arthritis in the rat

The following test shows the activity of the novel cationic salts of this invention against chronic inflammation in adjuvant induced arthritis which is accompanied by joint destruction. Groups of three Royal Hart, Wistar strain rats weighing 200±10 g. each were injected intradermally in the right hind paw with Freund's adjuvant (dried human tubercle bacilli in a mineral oil vehicle at a dose of 2 mg./kg. of body weight. The test compounds were administered orally in a 1.5% starch vehicle at various doses once daily on days 0 to 13 post challenge. Control rats were treated in a similar manner, but given only starch vehicle. On the 14th and 21st day post challenge the diameter of the injected paw was measured by micrometer caliper. The volume of inflamed paws were estimated from these measurements and the effects of each compound are expressed as percent inhibition of swelling was compared to controls. Table I records the results of these tests conducted with representative compounds of this invention and known anti-inflammatory agents. The active compounds of this invention suppress the progression of the arthritis and associated joint deterioration.

Table I

| Compound | Oral Dose (mg./kg.) | No. of Rats | (Primary Lesion) % Inhibition of Swelling | |
|---|---|---|---|---|
| | | | Day 14 | Day 21 |
| Normal Rats | — | 186 | — | — |
| Adjuvant Controls | — | 630 | 0 | 0 |
| Indomethacin | 2 | 57 | 51* | 24* |
| | 1 | 54 | 46* | 19* |
| | 0.5 | 54 | 40* | 20* |
| | 0.25 | 9 | 30* | 4 |
| Aspirin | 400 | 57 | 73* | 48* |
| | 200 | 66 | 48* | 27* |
| | 100 | 63 | 36* | 13 |
| | 50 | 21 | 23* | 3 |
| Phenylbutazone | 150 | 27 | 75* | 44* |
| | 75 | 39 | 62* | 28* |
| | 37.5 | 39 | 56* | 14 |
| | 18.5 | 21 | 31* | 7 |
| Benzoylacetonitrile sodium salt | 50 | 18 | 59* | 45* |
| p-Fluorobenzoyl-acetonitrile sodium salt | 50 | 18 | 53* | 32* |

*seg activity p = <.05 by t test

Adjuvant induced experimental polyarthritis is a specific systemic disease of the rat which shares interesting similarities with rheumatoid arthritis. Specifically the histology of the two diseases bears a remarkable resemblence as shown by C. M. Pearson et al., Am. J. Path. 42, 73 (1963). E. M. Glenn, Am. J. Vet. Res. 27, (116), 339 (1966) has classified adjuvant induced polyarthritis as a crippling and permanent deformity resulting from diffuse connective tissue involvement around certain susceptible joints in the rat. Zahiri et al, Can. Med. Ass. J., 101, 269 (1969) have shown that the fusiform swelling of the distal joints is associated with edema, congestion and synovitis including pannus formation, all of which precede the ultimate destruction of bone and cartilage. Furthermore, Zahiri et al., indicate that the cartilage destruction in the joint is due to an invasive pannus which originates in the marginal synovium and extends across the articular surface to erode it. When non-steroidal, anti-inflammatory agents such as indomethacin inhibit arthritic paw swelling, which is composed of inflammatory cell infiltrates, they have also been shown to prevent joint and bone deterioration [see S. Wong et al., J. Pharm. & Exp. Ther. 185, 127 (1973) and G. R. Bobalick et al., Agents and Actions 4, 364 (1974)]. The most pointed reference showing the relationship between arthritis and joint deterioration is an X-Ray analysis of adjuvant arthritis in the rat by Blackham et al., Agents and Actions 7, 145 (1977). In a similar manner, inhibition of the progress of arthritis in paws of rats treated with the compounds of this invention also lessens associated joint deterioration.

Compositions according to the present invention having the desired clarity, stability and adaptability for parenteral and intra-articular use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, phenyl mercuric nitrate, benzalkonium chloride, phenethyl alcohol, p-chlorophenyl-α-glycerol ether, methyl and propyl parabens, and thimerosal. As a practical matter it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel cationic salts are equally adapted to intravenous administration when diluted with water or diluents employed in intraveous therapy such as isotonic glucose in appropriate quantities. For intravenous use, initial concentrations down to about 0.05 to 0.25 mg./ml. of active compound are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

Benzoylacetonitrile, sodium salt

A 2.75 g. portion of sodium hydroxide and 11.5 g. of benzoylacetonitrile are added to 50 ml. of water. The mixture is stirred at room temperature for 3 hours, filtered, and the water stripped off. The residue is recrystallized from ethanol/n-hexane with cooling in a freezer overnight giving the desired product as a colorless solid.

EXAMPLE 2 o-Fluorobenzoylacetonitrile, potassium salt

The procedure of Example 1 is repeated substituting equimolecular amounts of o-fluorobenzoylacetonitrile and potassium hydroxide for the benzoylacetonitrile and sodium hydroxide employed in that example. There is thus obtained the potassium salt of o-fluorobenzoylacetonitrile in equally good yield.

EXAMPLE 3 p-Fluorobenzoylacetonitrile, sodium salt

A 3.0 g. portion of sodium hydroxide is dissolved in 50 ml. of water. A 15 g. portion of p-fluorobenzoylacetonitrile is added and the mixture is stirred for 2 hours at room temperature, filtered, washed with water and then the water is stripped off. The residue is recrystallized from ethanol/n-hexane giving the desired product.

EXAMPLE 4 m-Fluorobenzoylacetonitrile, magnesium salt

By replacing the p-fluorobenzoylacetonitrile and sodium hydroxide employed in Example 3 with equimolar amounts of m-fluorobenzoylacetonitrile and magnesium hydroxide, there is obtained the corresponding magnesium salt of m-fluorobenzoylacetonitrile.

EXAMPLE 5

| Preparation of 50 mg. Tablets | | |
|---|---|---|
| Per Tablet | | Per 10,000 Tablets |
| 0.050 gm. | benzoylacetonitrile, potassium salt | 500 gm. |
| 0.080 gm. | Lactose | 800 gm. |
| 0.010 gm. | Corn Starch (for mix) | 100 gm. |
| 0.008 gm. | Corn Starch (for paste) | 75 gm. |
| 0.148 gm. | | 1475 gm. |
| 0.002 gm. | Magnesium Stearate (1%) | 15 gm. |
| 0.150 gm. | | 1490 gm. |

The benzoylacetonitrile, potassium salt, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 6

| Preparation of Oral Suspension | |
|---|---|
| Ingredient | Amount |
| p-fluorobenzoylacetonitrile, calcium salt | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water    qs ad | 100 ml. |

The sorbitol solution is added to 40 ml. of distilled water and the p-fluorobenzoylacetonitrile, calcium salt is suspended therein. The saccharin, sodium benzoate, flavor and dye are added and dissolved. The volume is adjusted to 100 ml. with distilled water. Each ml. of syrup contains 5 mg. of p-fluorobenzoylacetonitrile, calcium salt.

EXAMPLE 7

Preparation of Parenteral Solution

In a solution of 700 ml. of propylene glycol and 200 ml. of water for injection is suspended 20.0 grams of o-fluorobenzoylacetonitrile, sodium salt with stirring. After suspension is complete, the pH is adjusted to 7.5–8.0 with sodium hydroxide and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 8

| Preparation of Topical Cream | |
|---|---|
| Ingredient | Amount |
| m-fluorobenzoylacetonitrile, triethylammonium salt | 1.0% |
| Ethoxylated stearyl alcohol | 10.0% |
| Benzyl alcohol | 0.9% |
| Isopropyl palmitate | 5.0% |
| Sorbitol solution (USP) | 5.0% |
| Glycerin | 5.0% |
| Triethylamine   qs to   pH 7.5–8.0 | |
| Water   qs ad | 100.0% |

The ethoxylated stearyl alcohol and isopropyl palmitate are heated to liquifying temperature. About 95% of the total volume of water is placed in a separate container followed by the glycerin and sorbitol solution. This aqueous mixture is brought to a boil and then cooled to 60°–75° C. The m-fluorobenzoylacetonitrile, triethylammonium salt is added to the wax phase and the mixture is stirred until a clear solution is obtained. The benzyl alcohol is added and dissolved in the wax phase. The water phase is passed through a screen into the wax phase while maintaining agitation. Both phases are kept at about the same temperature during transfer. The mixture is cooled while agitation is continued. At a temperature of 50°–55° C. the balance of the water is added. The batch is cooled with minimum agitation until the cream sets in its final form.

EXAMPLE 9

Preparation of Intra-articular Product

| Ingredient | Amount |
| --- | --- |
| benzoylacetonitrile, magnesium salt | 2-20 mg. |
| NaCl (physiological saline) | 0.9% |
| Benzyl alcohol N.F. | 0.9% |
| Sodium carboxymethylcellulose | 1-5% |
| pH adjusted to 7.5-8.0 | |
| Water for injection   qs ad | 100% |

EXAMPLE 10

Preparation of Injectable Depo Suspension

| Ingredient | % W/V |
| --- | --- |
| p-fluorobenzoylacetonitrile, benzyltrimethylammonium salt | 0.05-5 |
| Polysorbate 80 USP | 0.2 |
| Polyethylene glycol 4000 USP | 3.0 |
| Sodium chloride USP | 0.8 |
| Benzyl alcohol N.F. | 0.9 |
| Aqueous ammonia to pH 7.5-8.0 | qs |
| Water for injection   qs ad | 100.0 |

We claim:
1. The method of inhibiting the progression of arthritis in a mammal which comprises administering to said mammal an effective amount of a compound of the formula:

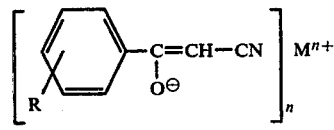

wherein R is hydrogen or fluoro, M is a pharmacologically acceptable cation, and n is an integer from 1 to 3.

2. The method of inhibiting progressive joint deterioration in a mammal which comprises administering to said mammal an effective amount of a compound of the formula:

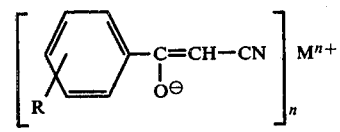

wherein R is hydrogen or fluoro, M is a pharmacologically acceptable cation, and n is an integer from 1 to 3.

3. The method of meliorating inflammation in a mammal which comprises administering to said mammal an effective amount of a compound of the formula:

$$\left[ \underset{R}{\underset{|}{\bigcirc}} - \underset{O^{\ominus}}{\overset{|}{C}} = CH - CN \right]_n M^{n+}$$

wherein R is hydrogen or fluoro, M is a pharmacologically acceptable cation, and n is an integer from 1 to 3.

* * * * *